US009310328B1

(12) United States Patent
Abdalla et al.

(10) Patent No.: US 9,310,328 B1
(45) Date of Patent: Apr. 12, 2016

(54) METHOD OF DETECTING LEUKEMIA

(71) Applicant: KING ABDULAZIZ UNIVERSITY, Jeddah (SA)

(72) Inventors: Soliman Mahmoud Soliman Abdalla, Jeddah (SA); Abdullah Yousif Obaid, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 14/742,618

(22) Filed: Jun. 17, 2015

(51) Int. Cl.
*G01R 27/08* (2006.01)
*G01N 27/06* (2006.01)
*G01N 27/07* (2006.01)

(52) U.S. Cl.
CPC ............... *G01N 27/06* (2013.01); *G01N 27/07* (2013.01)

(58) Field of Classification Search
CPC ...... G01N 27/02; G01N 27/026; G01N 27/04
USPC .......................................... 607/901; 324/691
See application file for complete search history.

(56) References Cited

U.S. PATENT DOCUMENTS

| 6,812,204 | B1 | 11/2004 | McHale et al. |
| 6,949,355 | B2 | 9/2005 | Yamanishi et al. |
| 2003/0015428 | A1 | 1/2003 | Becker et al. |
| 2003/0119057 | A1 | 6/2003 | Gascoyne et al. |
| 2009/0314644 | A1 | 12/2009 | Golan et al. |
| 2012/0237997 | A1 | 9/2012 | Koser |
| 2014/0172321 | A1* | 6/2014 | Han .................... G01N 15/1436 702/21 |
| 2015/0001083 | A1* | 1/2015 | Martin ............ G01N 27/44791 204/601 |

OTHER PUBLICATIONS

Iliescu, Ciprian et al., "Novel microfluidic device for cell characterization by impedance spectroscopy", Biomedical Applications of Micro- and Nanoengineering III, ed. Dan V. Nicolau, Proc. of SPIE vol. 6416, 64160F, (2006).*
Bernal-Alvarado, Jesus et al., "Characterization of Human Blood Tissue by Impedance Spectroscopy and Study of Erythrocyte Sedimentation", CP854, Medical Physics: Ninth Mexican Symposium on Medical Physics, ed. H. Mercado-Uribe et al., © 2006 American Institute of Physics.*
Becker, F. F. et al., "The removal of human leukaemia cells from blood using interdigitated microelectrodes", J. Phys. D: Appl. Phys 27, (1994), 2659-2662, © 1994 IOP Publishing, Ltd.*
Bernal-Alvarado, Jesus et al., "Dielectric Characterization of Leukocytes from Human Blood", CP854, Medical Physics: Ninth Mexican Symposium on Medical Physics, ed. H. Mercado-Uribe et al., © 2006 American Institute of Physics.*

(Continued)

*Primary Examiner* — Benjamin M Baldridge
(74) *Attorney, Agent, or Firm* — Richard C. Litman

(57) ABSTRACT

The method of detecting leukemia involves placing a suspension of red blood cells in a reservoir having a capillary tube partially immersed in the reservoir. An alternating current is applied to electrodes (one in the reservoir, the other in the capillary tube) at different frequencies. The electrical resistance is measured at the interface between the electrode and the suspension in the capillary tube. At the same time, CCD (charge coupled device) cameras take images, both top views and side views. The electrical resistance will show a peak at a characteristic resonant frequency, which is different for cancerous blood cells than for normal blood cells. The CCD images will show a pattern of maximum repulsion from the electrode at the resonant frequency in the top view, and minimum height of blood cells on the side of the electrode at the resonant frequency in the side view.

9 Claims, 11 Drawing Sheets

(56) References Cited

OTHER PUBLICATIONS

Zheng, Fan, "Investigation of Cancer Cell Indentification in Suspension by Bioimpedance Spectroscopy", A Disssertation submitted to the University of Sussex in partial fulfillment of the requirements for the degree of master of philosophy, Apr. 2012.*

Adrienne R. Minerick et al., "Manipulation and characterization of red blood cells with alternating current fields in microdevices", Electrophoresis (2003), vol. 24, pp. 3703-3717.

Adrienne R. Minerick et al., "Electrokinetic transport of red blood cells in microcapillaries", Electrophoresis (2002), vol. 23, pp. 2165-2173.

* cited by examiner

METHOD OF DETECTING LEUKEMIA

BACKGROUND OF THE INVENTION

1. Field of the Invention

The present invention relates to methods for separating microparticles, and particularly to a method of detecting leukemia by examining the resistance and electromagnetic repulsion of a suspension of red blood cells under the influence of an alternating current field.

2. Description of the Related Art

Leukemia is a disease that involves cancer of the blood cells or bone marrow. There are several forms of leukemia, most of which are characterized by the overproliferation of white blood cells, which are often abnormal or immature. Although the white blood cells are primarily affected, since leukemia also affects the bone marrow, red blood cells are also affected by the disease. Many forms of leukemia are amenable to treatment, and some forms may be completely cured. As with all forms of cancer, the key to effective treatment is early detection. Sadly, the American Cancer Society has estimated that one in every five cases of leukemia has not been diagnosed. There continues to be a need for methods of detecting the presence of leukemia.

Various techniques exist in the prior art to detect bio-fluid microparticles (MPs) such as blood. Indeed, extensive work has been presented to study the electrical behavior of microparticles (MPs) suspended through bio fluid. The prior art on nano-particles drug delivery consider liquids with "Newtonian-behavior" if they contain suspending MPs. However, this is not the case in most medical situations and can't be applied on most biological human-fluids such as blood. In fact, this vital fluid, i.e., blood is a very complex heterogeneous bio-fluid. It contains flexible and very deformable micro-cells, platelets, proteins, NPs suspended through plasma and therefore blood should not be considered as simple liquid. In particular, for blood flow in arterioles and venules, the particulate nature of the blood should be taken into account when thinking about drug delivery processes. The existence of the "cell free layer" and nano-particle-interaction drastically affects the binding rates and dispersions processes thereby influencing targeted delivery-efficiency. Electrical reactance measurements have been used to detect the presence of minute concentrations of bacteria at frequencies of about one mega Hertz. Also, previous research efforts have been directed to investigate the presence of AC-Faradic polarization using various metallic electrodes. However, electrical measurements of bio-fluid such as blood that comprises both MPs and NPs suspended still pose great challenges.

Thus, a method of detecting leukemia solving the aforementioned problems is desired.

SUMMARY OF THE INVENTION

The method of detecting leukemia involves placing a suspension of red blood cells in a reservoir having a capillary tube partially immersed in the reservoir. A first electrode is placed in contact with the surface of the suspension in the reservoir, and a second electrode is lowered into the capillary tube until it comes into contact with the surface of the suspension rising within the tube. An alternating current is applied to the electrodes at different frequencies. The electrical resistance is measured at the interface between the electrode and the suspension in the capillary tube. At the same time, CCD (charge coupled device) cameras take images, both top views and side views, at the interface between the electrode and the suspension in the capillary tube. The electrical resistance will show a peak at a characteristic resonant frequency, which is different for cancerous blood cells than for normal blood cells. The CCD images will show a pattern of maximum repulsion from the electrode at the resonant frequency in the top view, and minimum height of blood cells on the side of the electrode at the resonant frequency in the side view. Particularly, by applying an a.c. field to the electrodes and sweeping the frequency of the a.c. field between 0 Hz and $1 \times 10^7$ Hz, the electrical resistance is measured as a function of frequency at the interface between the second electrode and the surface of the suspension. One may then conclude that cancerous cells are present in the suspension when the resistance peaks at a frequency that is unique to red blood cells obtained from patients with leukemia.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The method of detecting leukemia involves placing a suspension of red blood cells in a reservoir having a capillary tube partially immersed in the reservoir. A first electrode is placed in contact with the surface of the suspension in the reservoir, and a second electrode is lowered into the capillary tube until it comes into contact with the surface of the suspension rising within the tube. An alternating current is applied to the electrodes at different frequencies. The electrical resistance is measured at the interface between the electrode and the suspension in the capillary tube. At the same time, CCD (charge coupled device) cameras take images, both top views and side views, at the interface between the electrode and the suspension in the capillary tube. The electrical resistance will show a peak at a characteristic resonant frequency, which is different for cancerous blood cells than for normal blood cells. The CCD images will show a pattern of maximum repulsion from the electrode at the resonant frequency in the top view, and minimum height of blood cells on the side of the electrode at the resonant frequency in the side view. The method will now be explained by the following experimental examples.

Figure 1:
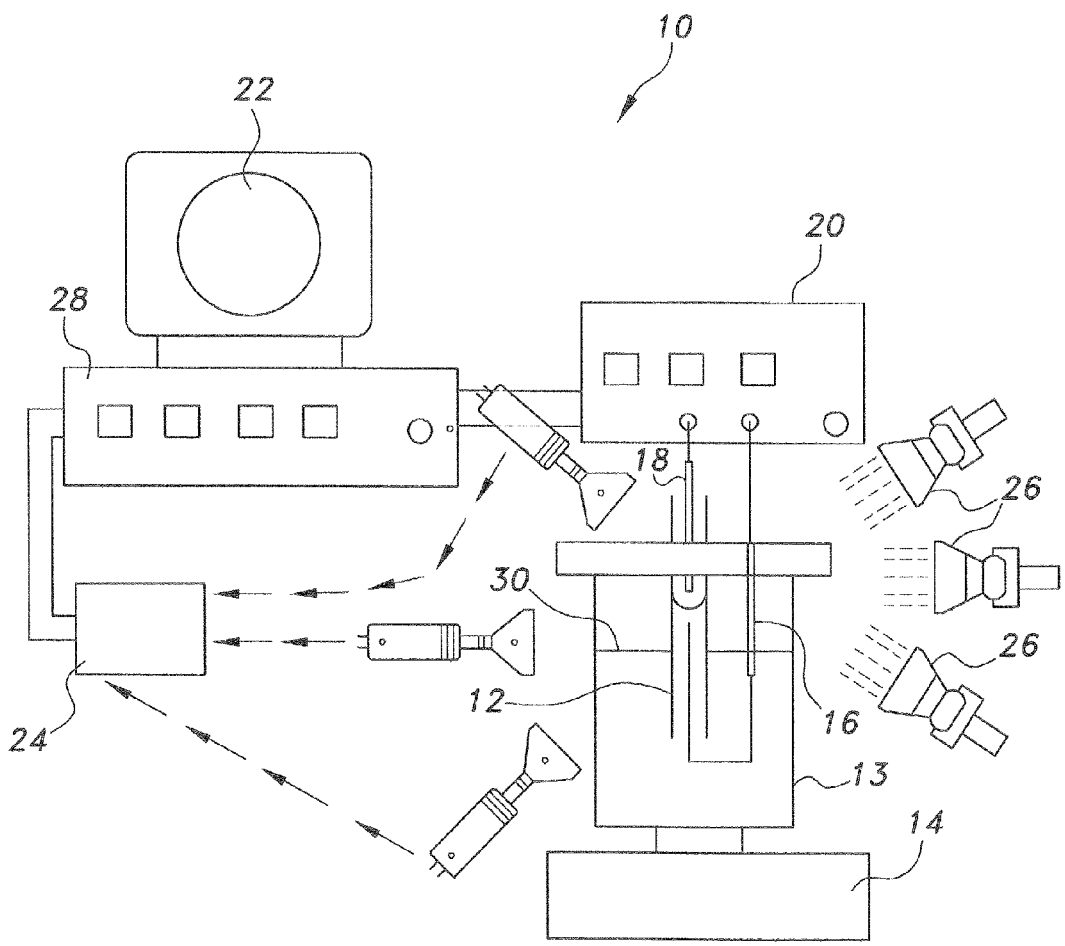
FIG. 1 is a diagrammatic elevation view of an apparatus for implementing a method of detecting leukemia according to the present invention.

To know what is electrically happening with microparticles in biosuspension (and particularly in water and blood); it is suggested to study the effect of applying an a.c. field to a fluid containing microparticles at specific conditions. The particles are in weak equilibrium mechanical conditions. For example, when fluid containing microparticles rises in a glass capillary tube (by surface tension forces), then a metallic electrode touches the upper surface of suspension, a microportion of fluid will be sandwiched between the surface of the liquid and the metallic electrode. In the small area between the liquid surface and the metallic electrode, microparticles will be under mechanical equilibrium between the upward surface tension forces and gravitational forces. This mechanical equilibrium is sensitive to any additional external forces, and it will be highly disturbed if an a.c.-electric force is applied. Due to the mechanical equilibrium, this behavior is more obvious in a capillary tube than if the microparticles are inside the bulk suspension. Thus, the present invention includes a configuration that is adapted, in particular, to study the a.c. electrical resistance (or impedance) as a function of frequency at the metallic electrode interface area. The apparatus 10 is shown in FIG. 1.

The measuring cell has a capillary glass tube 12 (open at both ends) that has a 100 μm radius, which is the central element of the setup, pinned in a beaker 13 or other reservoir filled with distilled water 30. The measuring compartment has been placed on a stage 14 movable with a micrometer screw. The immersion-depth of the capillary and the electrode has been controlled by the movable stage 14, which varies in the range between 5 and 15 mm with an accuracy of 1 μm. The measurements are started when lowering the metallic electrode in the capillary using the micro metrical screw to control the stage 14. Two events will happen when the electrode just touches the water surface: First, the electric current passes through an RCL-meter 20, and a monitor 22 shows mechanical contact between the microelectrode and the water surface. The time phase between the two events is considered to be zero. A CCD camera 24, which is illuminated with a cold light source 26, shows that the period of time necessary that water molecules with microparticles rise and stick to the capillary walls (and/or metallic surface) is by far inferior than the maximum efficiency of the CCD camera, which gives confidence to the measurements. A master computer 28 has been used to control both the images coming from the CCD camera 24 and the measurements coming from the RCL-meter 20, and to control values of frequency and voltage that is applied to the water/electrode surface.

The metallic electrodes 16 and 18 are made of 50 μm metal varnish-isolated wire, where the part that touches suspension or water 30 is a point contact of clean metal. Three types of metals have been used, including silver, platinum and copper. The electrode ends have been initially treated with diluted sulfuric acid solution (for copper and silver electrodes) and treated with aqua regia for platinum electrodes to soften and remove away non-uniform edges, if any. Thus, one will have symmetric electrode contact-points. Two metallic electrodes have been used. One electrode 16 is inside the beaker 13 and touches the suspension (or water) surface, and the other electrode 18 touches the suspension upper surface inside the capillary tube 12. When the metal electrode 18 just touches the suspension surface, microparticles will rise with the suspension up to adhere to metal (by surface tension and without application of an electric field).

During the measurements, the beaker 13 has been covered by a glass plate to prevent evaporation, which can lead to change of the water level and to development of a temperature gradient normal to the surface due to cooling of the upper surface. The electrical resistance R of the micro-suspension sample inside the capillary 12 has been measured as a function of frequency at a constant electric potential (0.5 volt). Another series of experimental measurements (resistance) have been carried out at a constant frequency (the critical frequency) as a function of the applied electric potential in volts. The electrical conductivity and the dielectric constant have not been recorded because of the difficulty of determination the effective contact-area with reasonable tolerance. Ultrapure de-ionized water with a conductivity of $5.5 \times 10^{-8}$ $\Omega^{-1}$ cm$^{-1}$ produced by "pure lab plus" has been used as reference. All measurements have been carried out at room temperature at the suspension (or water) surface. When they are prepared for electrical measurements, the active-microparticles have been maintained on nutrient agar slants at 27° C. in order to maintain its biological activity. The number of microparticles has been manually counted on frozen camera frame when active microparticles form an aggregation. Data analysis has been carried out by analyzing microparticles with the camera, frame-by-frame. Pixel positions in an x- and y-level have been obtained at the cell center in each frozen video frame.

Electrical resistance measurements up to $10^7$ Hz have been performed using frequency-response analyzers (Novo control BDS-40 and Schluberger-1260). The suspension surface and the metallic electrode sandwiches the sample, which makes a condenser of parallel plate configuration. Digital output (electronic files) have been connected to Japan Victory Company video-recorder (HR-S9800U). This recorder divides the signal to a TV and a computer with an ATI-All in Wonder 128 PRO-32MBAG-Video Card TV Tuner & Capture. Tektronix oscilloscope-2205 has been used to monitor the electric signals.

In the present work, we provide surface electrical resistance for the following samples: 1—tap water; 2—Normal RBCs-N cells suspended in distilled water; 3—malignant RBCs cells (leukemia cells RBCs-L) suspended in distilled water; 4—Yeast suspended in distilled water; and 5—*Escherichia coli* (*E. coli*) bacteria suspended in distilled water.

Fresh human normal-blood (i.e., blood without disorders) has been obtained via venipuncture and stored in vacutainers with 1.8 mg K2 EDTA per ml of blood. Until use, whole blood has been stored at 4° C. using a refrigerator. Isotonic phosphate buffered saline (140 millimoles of sodium chloride, 25 millimoles of mono-potassium phosphate, and 9.1 millimoles di-potassium phosphate) has been used to dilute (1:400 ratio) standard concentrated RBCs-N(N means RBCs from normal blood) sample to obtain a final conductivity about 0.1 Ohms/m at 27° C. and a pH value 7.1. RBCs-N have been allowed to dissolve in such a way to obtain microparticle samples from the middle of the RBCs-N bottom layer. Thus, the cells have been kept in a balanced salt solution, and the ionic strength and distributions have been kept ideal for double layer effects and electrode surface. To minimize the electrode effect, we have used polystyrene latex particles of 5 mm. This buffer solution is suitable to examine the ionic movement phenomena because it is dominated by a 1:1 electrolyte with disparate diffusivities from the phosphate salts, which makes it easy to well recognize polarization mechanisms through double layer around the metallic electrode, if any. For RBCs-N, the phosphate buffer saline is a suitable solution to provide a physiologically balanced medium.

A sample of malignant leukemia cells (K-625RBCs) has been centrifuged, re-suspended in RPMI 2640 (Gibco-Invitrogen, Carlsbad, Calif.) supplemented with 10% fetal bovine serum, then stored in a refrigerator until used. Initially, before experimental runs, the cells have been centrifuged and washed several times, then suspended in phosphate buffer saline as it has been shown when preparing normal RBCs-N.

A sample of *Saccharomyces* cerevisiase (yeast cells) have been grown in shaken cultures at 27° C. in an environment containing 10 gram yeast extract, 20 grains D-glucose/liter and 10 gram polypepton. Yeast-cells have been collected at their early-stationary phase; treated several times with distilled water, then suspended in potassium chloride solution in concentrations within the range 0.01 mole<C<0.08 mole. The yeast-suspension has been incubated for about 90 minutes in order to get an ionic balance between the inner and the outer phase. Then, after the incubation, the collected yeast-cells have been re-suspended in a potassium chloride solution containing 0.1% agar, which is used to inhibit the cells sedimentation during the electric measurements, but it has no action on the electrical conduction of the medium.

The strain of *E. coli* used in the present study is *E. coli*-ATTC® 25922. Starting with one milliliter of overnight cultures grown in a 100 milliliter Erlenmeyer flask at 35° C. (without any agitation); these cells have been inoculated in 100 milliliter of Trypetic Soy Broth and incubated for live hours (without agitation) at 35° C. Cells are finally suspended in a 10 milliliter phosphate buffer solution prepared as previously shown.

Figure 2:
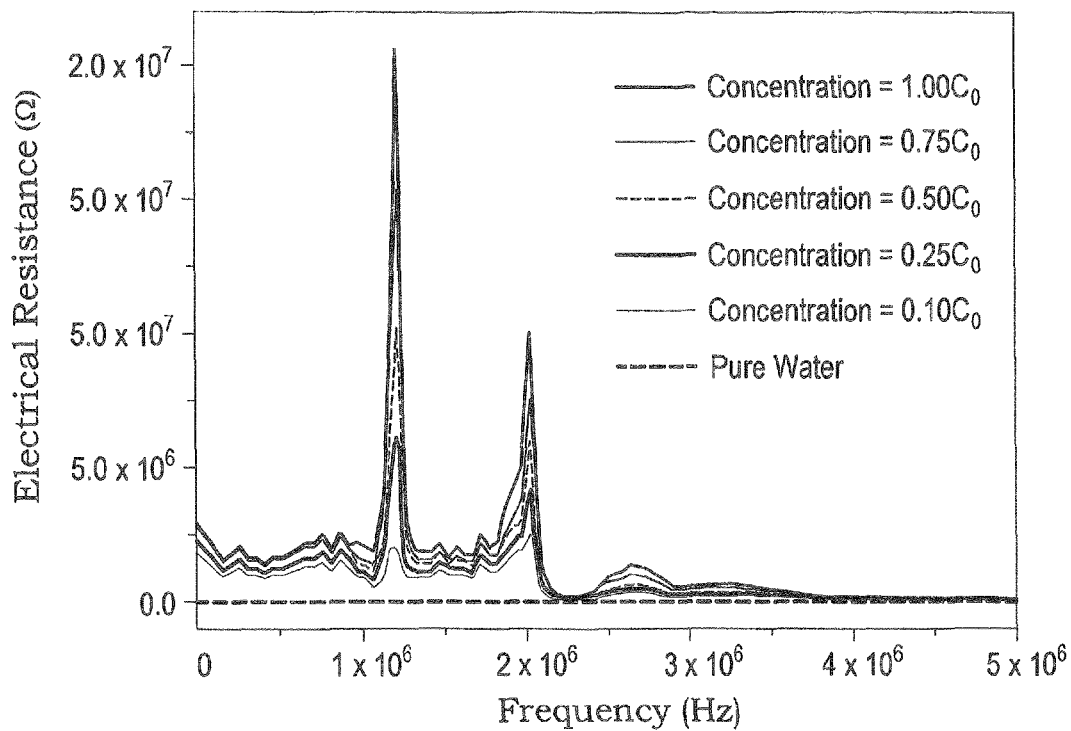
FIG. 2 is a graph of electrical resistance as a function of frequency, comparing distilled water to various concentrations of yeast.

As seen in FIG. 2, for distilled water, there is very weak dependence of the electrical resistance R on the frequency. However, when adding a certain concentration of yeast (c=0.52 gL$^{-1}$) to the distilled water, three peaks have been detected, at $1.21 \times 10^6$ Hz, $2.02 \times 10^6$ Hz and $2.62 \times 10^6$ Hz. The corresponding electrical resistances are: R=$20.7 \times 10^6$ Ω, $10.1 \times 10^6$Ω and $1.37 \times 10^6$Ω, respectively. When repeating the cycle of measurements at the same concentration c and at the same physical conditions, one gets the same values of data for several cycles. But when repeating the runs with different concentrations c, one finds that R increases with the concentration as R=$R_0$ exp(c/$c_0$), where $c_0$ is a constant that equals 0.52 gL$^{-1}$ and c is taken relative to $c_0$ as 0.1$c_0$<c<0.9$c_0$.

Figure 3:
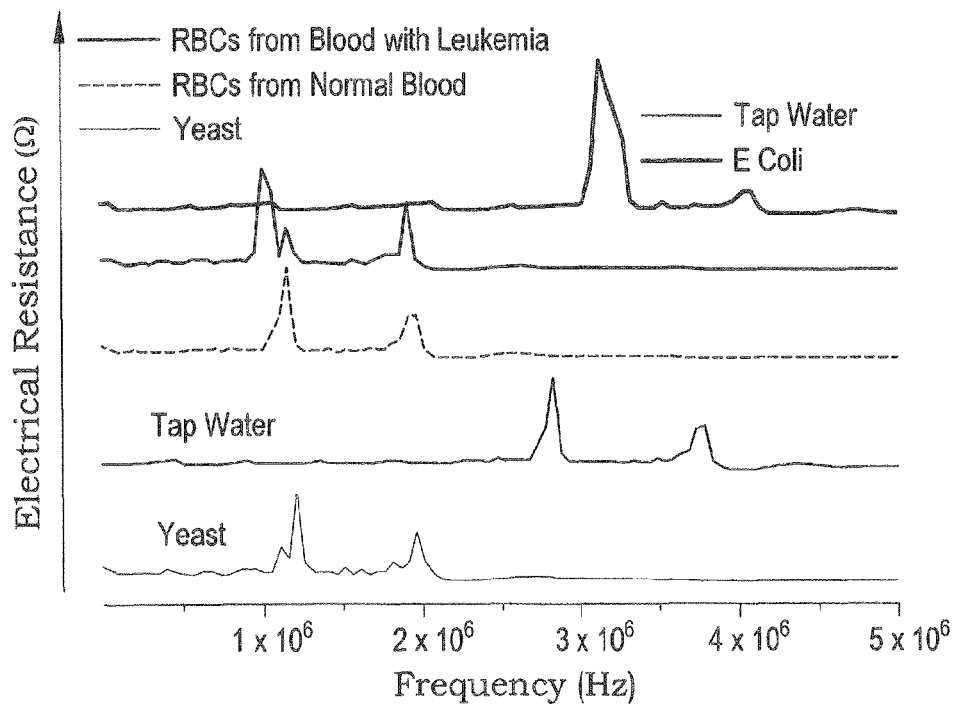
FIG. 3 is a graph of electrical resistance as a function of frequency, comparing tap water to suspensions of yeast, *E. coli*, normal red blood cells, and red blood cells from a patient with leukemia.

For other types of microparticles, the same phenomenon has also been observed. FIG. 3 shows the a.c. electrical resistance of RBCs-N suspended in distilled water as a function of frequency. One can see that the R-f curve has two net peaks at critical frequencies $(f_{01})_{RBCs-N}$=$1.2 \times 10^6$ Hz and $(f_{02})_{RBCs-N}$=$1.9 \times 10^6$ Hz, while for leukemia RBCs-L, the curve has two peaks at different critical frequencies, $(f_{01})_{RBCs-L}$=$9.1 \times 10^5$ Hz and $(f_{02})_{RBCs-L}$=$1.9 \times 10^6$ Hz. Similarly, in the same figure, tap water shows two peaks at critical frequencies $(f_{01})_{Tap\ water}$=$2.8 \times 10^6$ Hz and $(f_{02})_{Tap}$=$3.61 \times 10^6$ Hz. Moreover, *E. coli* cells have two peaks at critical frequencies $(f_{01})_{E\ Coli}$=$1.97 \times 10^6$ Hz and $(f_{02})_{E\ Coli}$=$3.18 \times 10^6$ Hz and yeast cells have two peaks at critical frequencies $(f_{01})_{Yeast}$=$1.9 \times 10^6$ Hz and $(f_{02})_{Yeast}$=$1.21 \times 10^6$ Hz.

Figure 4A:
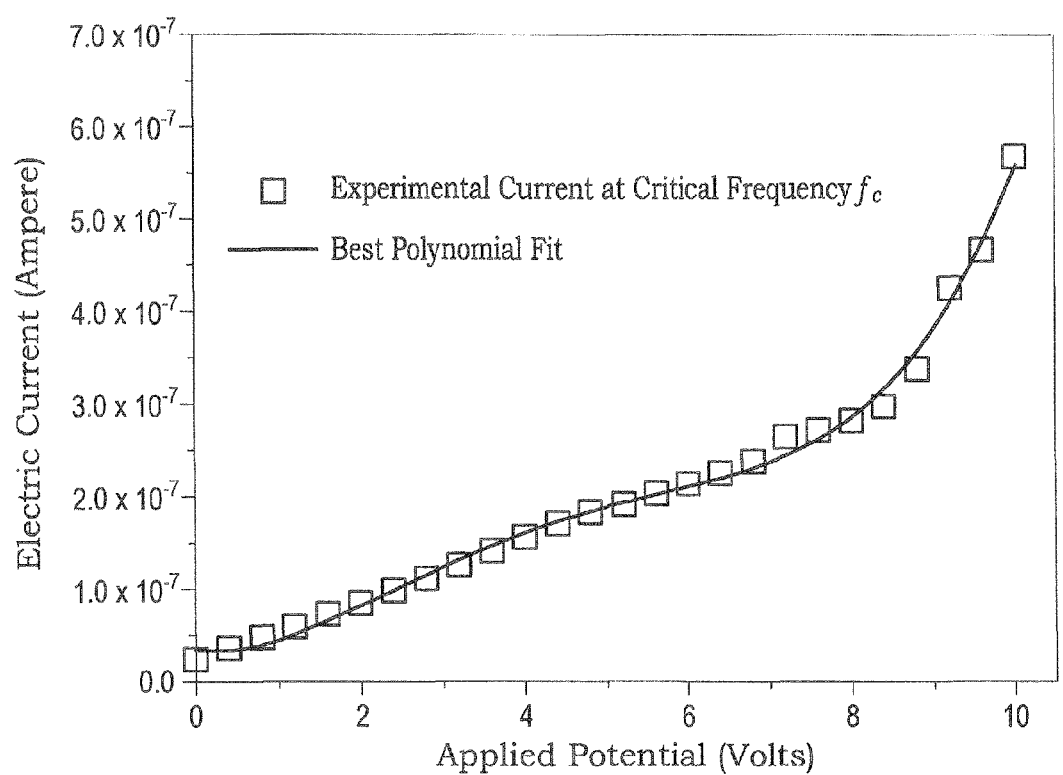
FIG. 4A is a plot of current as a function of applied voltage at the resonant frequency for a suspension of red blood cells from a patient with leukemia.

To investigate the effect of an a.c. field on electrical conduction by microparticles at the water/electrode interface, another series of measurements have been carried out on suspension of RBCs-N at a constant frequency $(f_{01})_{RBCs\ N}$=$1.2 \times 10^6$ Hz as a function of the applied electric potential. FIG. 4A shows the electrical current passing through the suspension of RBCs-L in distilled water as a function of applied potential V in volts. One can see a sudden increase of the current at a potential of about 8.4 volts. Moreover, we have found that the critical frequencies are insensitive to the electrode nature (at a condition that both electrodes have similar nature to prevent the Faradic Effect), i.e., the electrical resistance peaks are found at the same values whatever the nature of metallic electrode (at the same physical conditions).

Figure 4B:
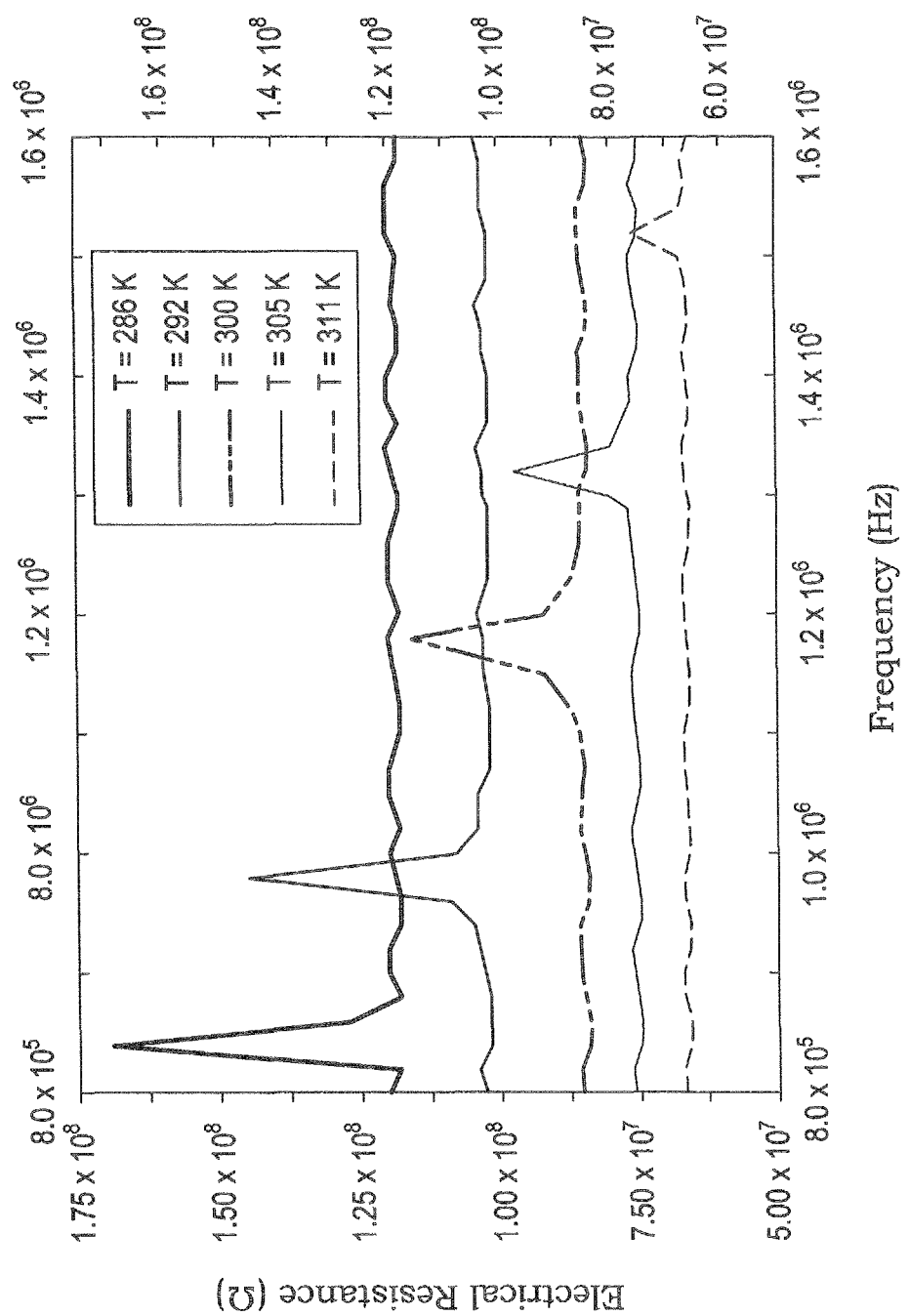
FIG. 4B is a graph illustrating the variation of electrical resistance as a function of frequency for different temperatures (T): (a) $f=8.4 \times 10^5$ Hz (286 K), (b) $f=9.8 \times 10^5$ Hz (292 K), (c) $f=1.18 \times 10^6$ Hz (300 K), (d) $f=1.3 \times 10^6$ Hz (305 K), and (e) $f=1.52 \times 10^6$ Hz (311 K).
Figure 4C:
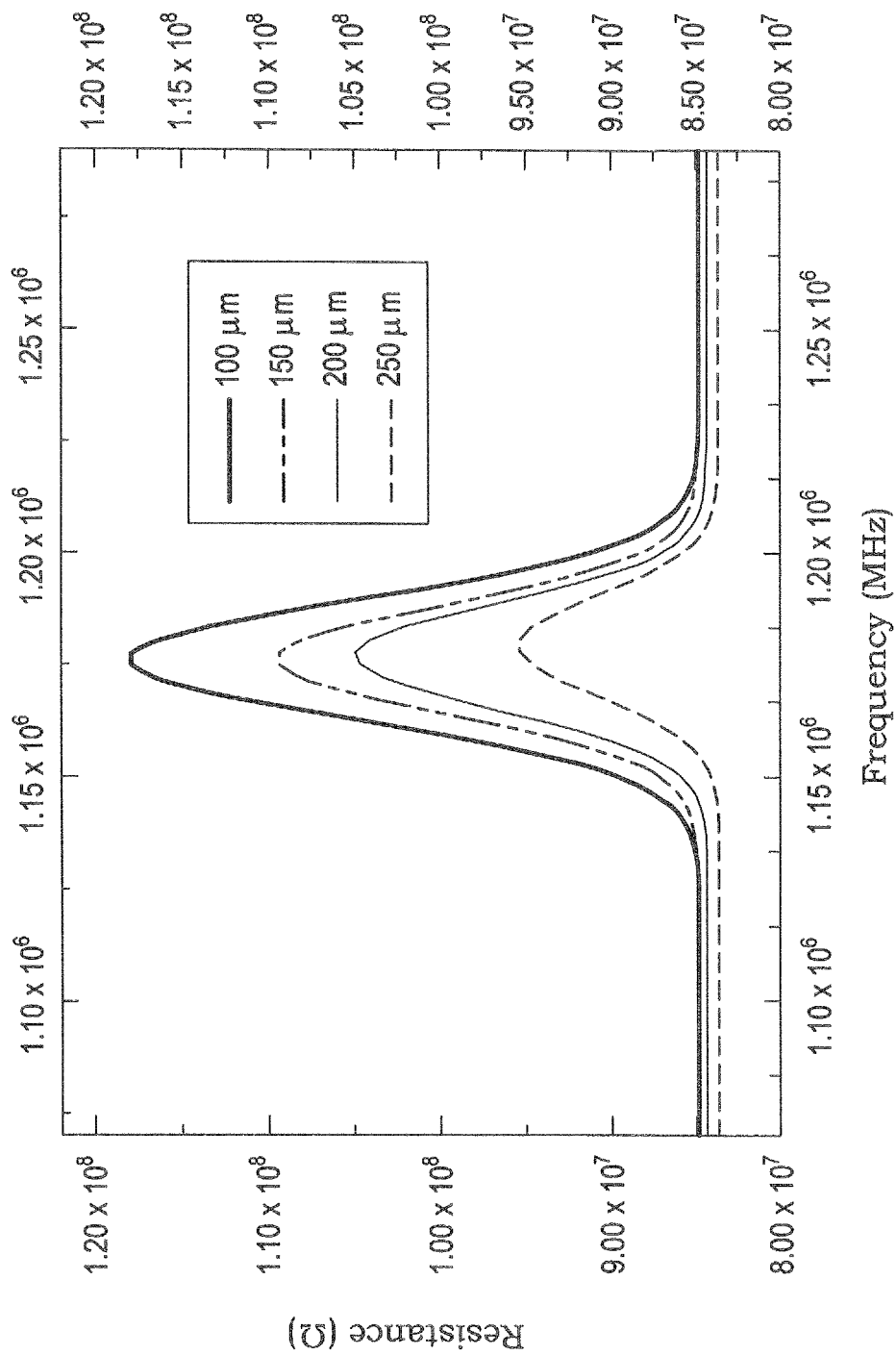
FIG. 4C is a plot of the variation of electrical resistance as a function of frequency for different capillary radii ranging from (a) 100 µm, (b) 150 µm, (c) 200 µm, and (d) 250 µm.

In order to verify that these experimental data are due to microparticles themselves and not due to other effects such as manipulation set up effects, we have measured the electrical resistance of N-RBCs suspended in distilled water as a function of frequency for different temperatures. FIG. 4B illustrates the variation of electrical resistance as a function of frequency for a suspension of RBCs-N in distilled water for different temperatures: (a) f=$8.4 \times 10^5$ Hz (286K), (b) f=$9.8 \times 10^5$ Hz (292 K), (c) f=$1.18 \times 10^6$ Hz (300K), (d) f=$1.3 \times 10^6$ Hz (305K), and (e) f=$1.52 \times 10^6$ Hz (311K). As is evident from FIG. 4B, there is a net displacement of the peak-resistance with temperature (T). Also, a net attenuation of the peak-resistance with temperature is observed. Examination of the frequency displacement with temperature in FIG. 4C shows that the critical frequency varies exponentially with temperature as expressed by the equation: $f_0=f_{00} \exp(-C_f/T)$. A similar behavior occurs for the resistance-peak, i.e., a regular exponential decrease of R with temperature as expressed by the equation $R=Ro \exp(-c_R/T)$.

Figure 4D:
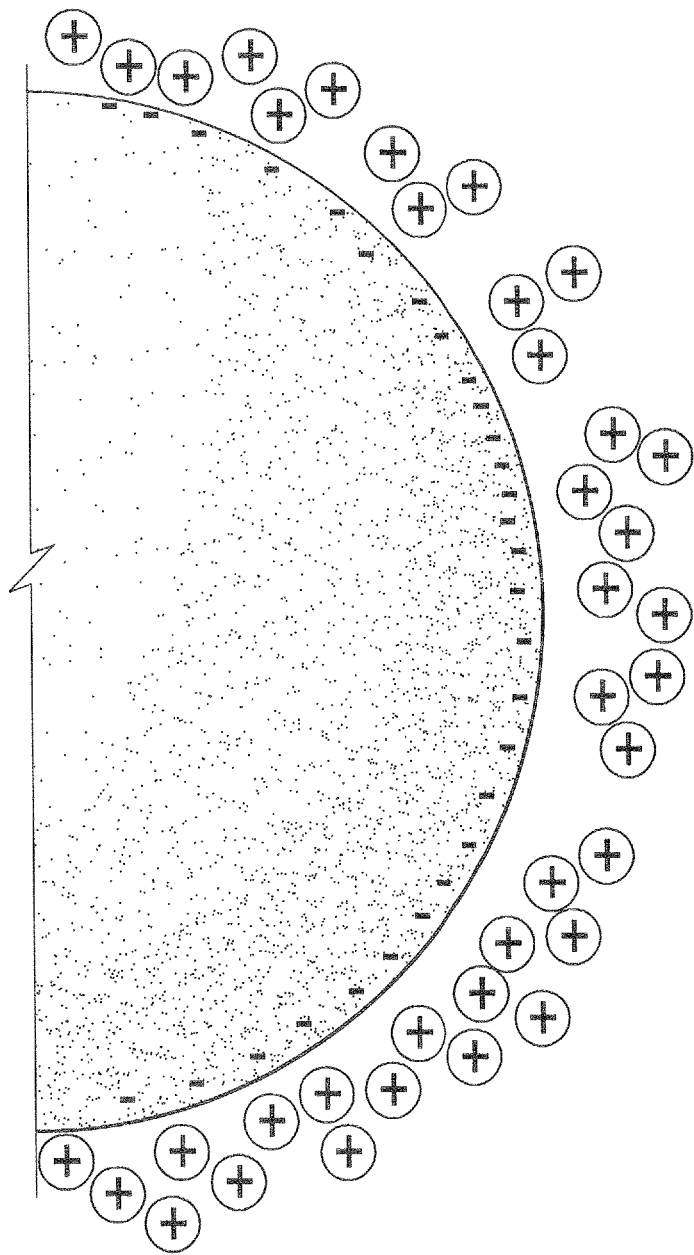
FIG. 4D shows the distribution of nano-particles (NPs) shown with positive charges around a negative red blood cell (RBC) which is taken in a first approximation as a sphere.

We believe that the effect of repulsion of microparticles (MPs) far from the metallic electrodes is due to a new phenomenon and not due to the well-known dielectrophoresis forces. To verify this hypothesis, we have measured the electrical resistance at the critical frequency as a function of the capillary radii, "r". As displayed in FIG. 4D, a net linear decrease of the peak-resistance occurs with increasing "r" as shown in the following equation: $R_{peak}=R_{peak0}-0.16$ r. The net dependence of the peak-resistance on frequency and temperature reveals that this phenomenon is really due to the MPs themselves and not to other effects (for example, dielectrophoresis forces, ac-Faradic polarization in micro devices, high intensity nonlinear electro-osmotic micro-vortex, hysteresis due to transient effects, etc.) As discussed above, FIG. 4B reveals net displacements of the peak-resistance with temperature. Attentive examination of the peak-resistance attenuation with temperature reveals that: $R=R_0 \exp(\Delta E_{CR}/T)$, with $Ro=Q$ and $-\Delta E_{CR}=0.18$ eV. A person of skill in the art can understand this temperature dependence when considering two layers of charges on the red blood cell (RBC), one is intrinsically present (negatively charged with potential −17 mV) and another positive layer of charged nanoparticles surrounded the negative ones, which is shown schematically illustrated in FIG. 4D.

The electric resistance of each layer follows thermally-activated behavior of each layer and the MW resistance of two-layer system can be characterized by a simple exponential relation with activation energy of 0.18 eV as the experimental data have given above. Also, there is a net displacement of the peak-frequency accompanied to the attenuation of the peak-resistance with temperature. This could be explained in terms of the increasing of relaxation time of MPs with temperature.

Figure 6:
FIG. 6 is a CCD image (top view) showing normal red blood cells in the suspension surrounding the electrode in the capillary tube at frequencies of $1.5 \times 10^6$ kHz, the red blood cells being repelled from the electrode and where some red blood cells form several pearl-like chains ranging up to six cells in length.
Figure 7:
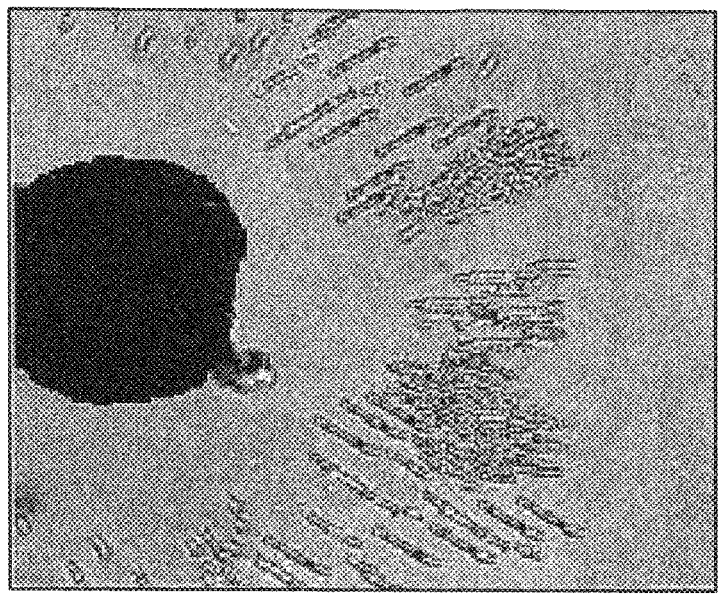
FIG. 7 is a CCD image (top view) showing normal red blood cells in the suspension surrounding the electrode in the capillary tube at frequencies of $1.65 \times 10^6$ kHz, the red blood cells showing maximum repulsion from the electrode and maximum chain formation.
Figure 8:
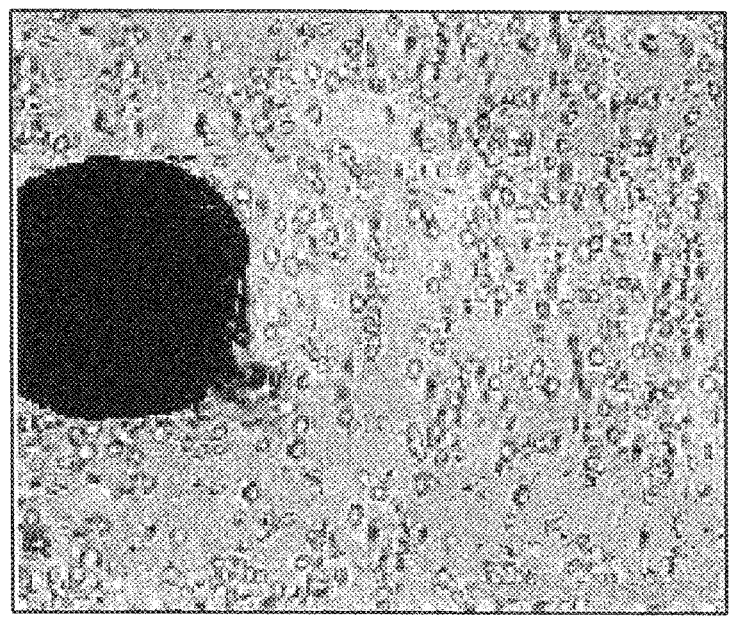
FIG. 8 is a CCD image (top view) showing normal red blood cells in the suspension surrounding the electrode in the capillary tube at frequencies of $1 \times 10^7$ kHz, the red blood cells having returned to a random distribution with the increase in frequency.

From the data in FIGS. 6 and 7 as shown infra; the repulsion of RBCs away from the metallic electrodes occurs when the applied electric frequency approaches from the critical frequency of RBCs-N. This has been demonstrated, also, by another experimental measurement. FIG. 1 shows that the electrical resistance of RBCs-N suspension suffers a sudden peak at $f_{ORBCS-N}=1.2 \times 10^6$ Hz and FIG. 6 shows that the repulsion of RBCs-N attains its maximum when forming several "pearl-like" chains at $1.65 \times 10^6$ Hz. Also FIG. 7 demonstrates that the rise of micro-particles attains its minimum rise when, $f_{ORBCS-N}=1.5 \times 10^6$ Hz. There is good matching between these frequency values and it means that at around $1.5 \times 10^6$ Hz the RBCs-N are in resonance with the external ac-field.

In order to be sure that the experimental data in the present invention are not due to dielectrophoresis forces it has been shown from FIG. 4C that the resistance-peak disappears when r>0.1 mm but dielectrophoresis forces are present if r>1 cm which sheds light on the contention that the resistance-peak is not due to dielectrophoresis forces. Additionally, there is a net displacement of the peak-frequency accompanied to the attenuation of the peak-resistance with temperature. This effect could be explained in terms of increasing of relaxation time of MPs with temperature as shown in references.

In order to check whether electrode polarization effects influence the present experimental data, it is well known that in strong ionic conductivity bio-fluids that contain suspended MPs (such as blood); the ions accumulate in thin layers at the electrodes immediately when applying low frequency (inferior than 1 kHz) ac-current. The phenomenon under investigation happens in the range of 1 MHz, which is very far from the effect of electrode polarization.

Figure 4E:
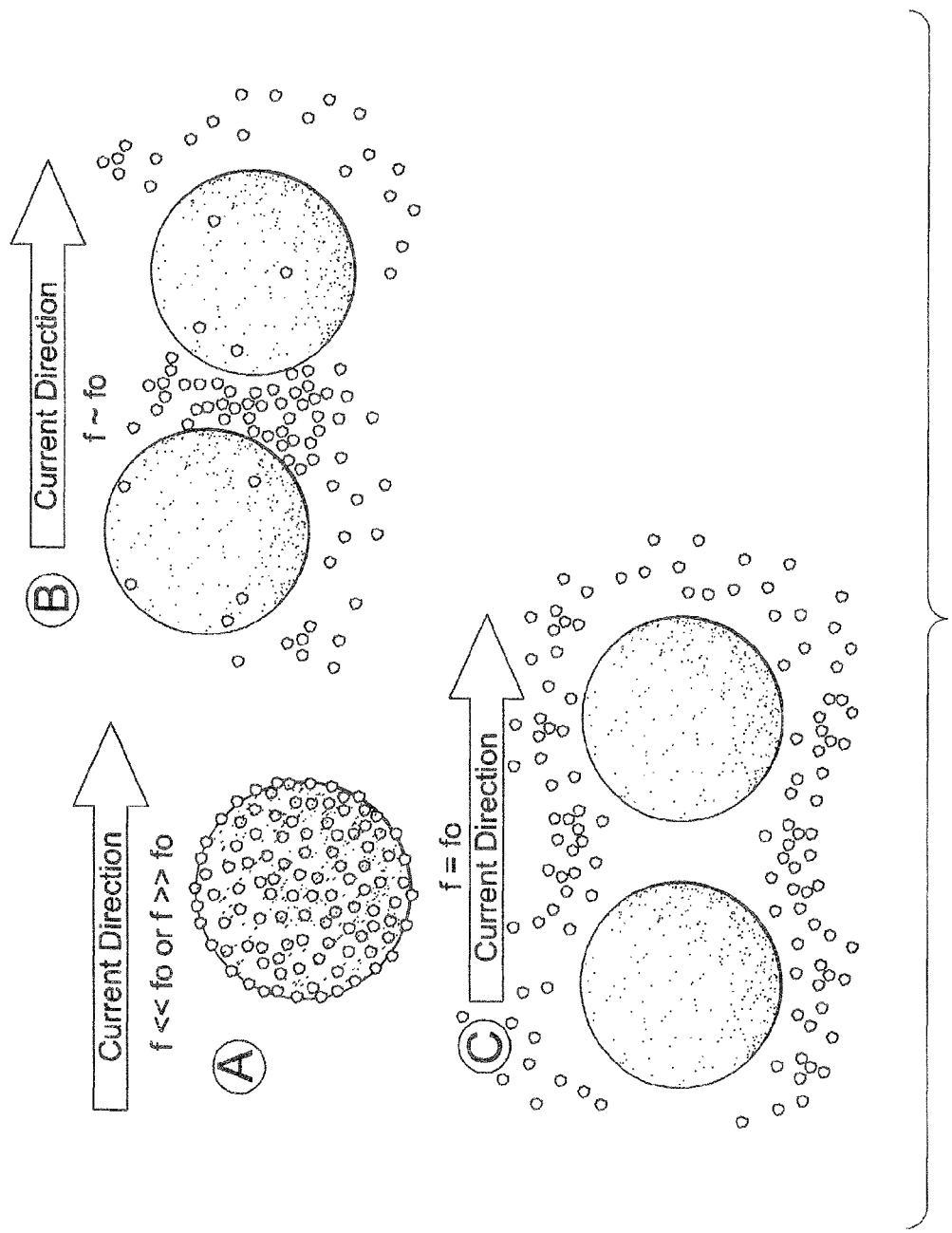
FIG. 4E shows schematically (A) the distribution of nano particles (NPs) at the surface of micro particles, e.g., red blood cell (RBC); (B) the NPs are well attracted to the red blood cell when applied electric frequency "f" is by far smaller than or greater than the intrinsic frequency of the micro particle itself $f_0$, i.e., when $f \ll f_0$ or when $f \gg f_0$; and (C) the external AC-field with frequency at "$f_0$" cleans out all the NPs from the surface of the micro particle.

In order to explain the synchronized increase of electrical resistance with the alienation away of MPs from the metallic electrode we start with the idea of "nano-sponges" as postulated by Adrienne et al. Adrienne et al. have considered NPs to be attached to red blood cell membranes. This scenario is schematically presented in FIG. 4E, portion "A", noting that others have shown that circulation of RBCs themselves is not affected by NPs attachments. These nanoparticles are considered to be positively charged and then attached to the negatively charged RBCs-N. The attraction forces are considered to be weak because the magnitude of positive charges is by far weaker than the negative charges on RBCs-N. Also, the attraction force is so weak that NPs will be immediately wiped up from the MPs-surfaces when resonance between external electrical frequency is matched with the natural frequency of MPs as illustrated in FIG. 4E, portions "B" and "C".

When an external ac-electric field is applied with a frequency equal to the natural frequency of the MPs, $f_0$, resonance will occur between the applied electric energy and the oscillating MPs. This resonance will supply mechanical energy to MPs which is sufficient to wipe out the attracted NPs as shown in FIG. 4E, portions "B" and "C". Thus, at $f_0$, MPs are without attracted NPs. The sudden cleaning out of NPs from the surface of MPs, as shown in portion "C" of FIG. 4E, results in two effects. First, if MPs are far from the metallic electrodes, they will suffer a sudden decrease in the effective surface-area of the electrical conduction, which will reduce the electrical conduction resulting in sudden increase in the electrical conductivity. Second, if MPs are near the metallic electrodes, the sudden wipe out of NPs will reduce the positive charges on the surface which will results in a sudden repulsion from the negative electrode. Denoting the sudden increase of resistance $R_{resonance}$, one can write the measured electrical resistance of RBCs-N suspended in distilled water as: $R_{measured}=R_{resonance}+R_{bulk}$; where $R_{bulk}$ is the electrical resistance of the bio-fluid.

The bulk resistance could be calculated based on the previous work of the present inventors, which shows that the applied field oscillations generate a charge density profile which creates equilibrium states between the electrostatic interactions and the thermal agitations during one complete cycle. If we consider that suddenness mechanical-shock occurs when resonance takes place between the external field-frequency and the intrinsic frequency of the micro-particle itself; i.e., when f=fo occurs at the MPs resonance, thus the relaxation time, $\tau$ of the particles could be given by the equation: $\tau_{Mps}=T_{Mpso} \exp(\Delta E\tau/kT)$ where k is the Boltzmann constant.

Thus, the application of an ac-field will stimulate the charged particles to keep their electrochemical potential against the field and the thermal agitations. Thus, with this pattern and with the principal of conservation of charges, one of skill in the art expects that under the application of an ac-electric field, the electrical conductivity $\sigma(\omega)$ will vary with angular frequency ($\omega$) and relaxation time of micro particles. This results in electrical resistance of the bulk medium as expressed by equation (1):

$$\sigma = \sigma_{MPs} + \frac{(\varepsilon_{sW}-\varepsilon_\infty)}{1+\omega^2\tau_{MPs}^2} \cdot \omega^2 \tau_{MPs} \qquad (1)$$

We use the above equation (1) to obtain the measured resistance with bulk resistance as a function of frequency and the measured resistance $R_{measured}$ could be given as shown below in equation (2):

$$R_{measured} = \frac{R_{0resonance}e^{c_{peak}/kT}}{1-\left(\frac{f}{f_0}\right)^2} + \frac{c_{cell}}{\sigma_{MPs} + \frac{(\varepsilon_{sMPs}-\varepsilon_{\infty})}{1+\omega^2\tau_{MPs}^2} \cdot \omega^2\tau_{MPs}e^{(\Delta E_\tau/kT)}} \quad (2)$$

The fitting parameters are as follows: the dc-current measured at dc-conditions $\sigma_{MPs}$=0.35 $\Omega^{-1}$ m$^{-1}$; the dielectric constant at very low frequencies $\varepsilon_{MPs}$=510 $\varepsilon_0$; the dielectric constant at very high frequencies $\varepsilon_{\infty}$=88 $\varepsilon_{\infty}$; relaxation time of MPs at 300 K, $\tau_{MPS0}$=8.2×10$^{-9}$ seconds; $R_{0resonance}$=1.5×10$^6$Ω, $c_{peak}$=55 meV, $\Delta E_\tau$=72 meV, $c_{cell}$=5× 10$^6$ m$^{-1}$. With these parameters we have found the best fitting between experimental data to equation (1). The additional attracted nano-particles that increase the resistance explains why others have found that electric induced dipoles of nano-collides are one order stronger than predicted by the classical Maxwell-Wagner theory and its extensions because at higher frequencies, the ac-period is too small for charging current to reach the charged layer between nano and micro-particles which decreases the space charge. However, at nearly 1 MHz, the electric field around the MPs has very high values because charge density of nano-particles becomes dramatically higher due to Stern-layer creation.

We have noticed that the critical-frequency values of RBCs-N($f_{c1}$)$_{RBCs-N}$ and ($f_{c2}$)$_{RBCs-N}$ are independent of the variation of the RBCs-N concentration. This behavior is repeated also for other microparticles, including RBCs-L and yeast cells. Moreover, these critical frequencies are insensitive to the electrode nature, i.e., the electric resistance peaks are found at the same values, regardless of the type of metallic electrode (silver, platinum, or copper) under the same conditions.

Figure 5:
FIG. 5 is a CCD image (top view) showing random distribution of normal red blood cells in the suspension surrounding the electrode in the capillary tube at frequencies of 0 Hz up to 150 kHz.

In order to know why the values of microparticles (for example yeast ($f_{01}$)$_{Yeast}$, FIG. 2) are insensible to the variation of the yeast concentration, another experimental set up has been constructed using three perpendicular cameras positioned in the x-, y- and z-directions around the capillary tube to get images for microparticles around the metallic electrode. At different frequencies, the cells of RBCs-N located in the glass capillary (in particular at the interface between the metallic contacts and solution) have been imaged in the z-direction (top view) and in the horizontal level, i.e., the x- and y-planes (side views). FIGS. 5 through 8 show the relative position of RBCs-N(top view) with respect to the metallic contact (appears as black area) at different frequencies. Generally, the red blood cells moved from a random distribution around the electrode 18 with no a.c. field (or a very low frequency a.c. field), gradually assuming a more ordered disposition in chains of cells repelled from the electrode up to a maximum critical frequency, and then gradually dispersing again to resume a random distribution with a further increase in the frequency of the applied a.c. field as the frequency is swept from 0 Hz to 1×10$^7$ Hz. FIG. 5 shows the random allocation of RBCs-N around the electrode 18 when there is no electric field, which is maintained for all frequencies in the range 0≤f<150 kHz. Above 150 kHz, the RBCs-N start to alienate away from the metallic contact. Net repulsion of RBCs-N continues with increasing frequency. This repulsion increases with frequency till 1×10$^6$ Hz. At 1.5×10$^6$ Hz, some RBCs-N form several pearl-shape chains ranging up to a maximum of six cells in length, as shown in FIG. 6. The formation of these chains increases and arrives at its maximum when the frequency attains 1.65×10$^6$ Hz, as shown in FIG. 7. At 2×10$^6$ Hz, the formation of these chains decreases rapidly, and RBCs are again aligned around the metallic electrode 18. As the frequency continues to increase, the chains continue to break up and the red blood cells assume a more random configuration, so that at 1×10$^7$ Hz, the cells appear to have a random distribution (shown in FIG. 8) similar to the original configuration shown in FIG. 5. At first sight, the disordered distribution of RBCs-N around the metallic electrode has two maxima, which occur at both frequency limits, at zero and at 1×10$^7$ Hz. The minimum disorder takes place at 1.65×10$^6$ Hz, corresponding to the maximum order-scale of "pearl-like chains" of microparticles.

Figure 9:
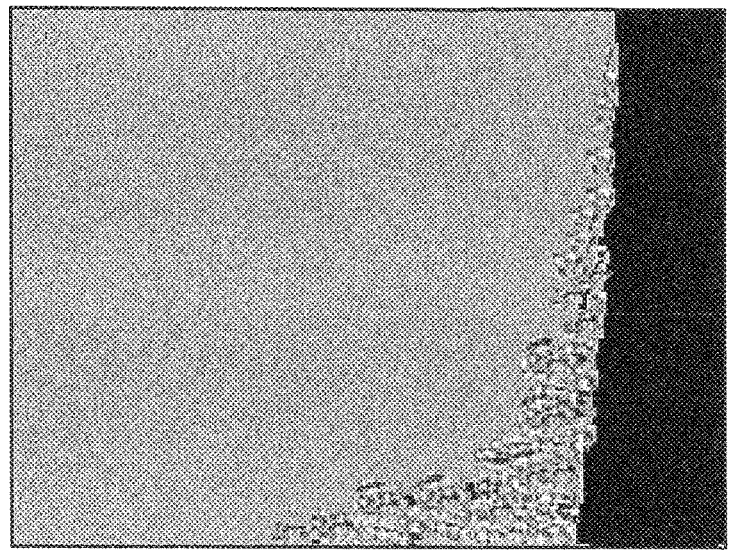
FIG. 9 is a CCD image (side view) showing random distribution of normal red blood cells in the suspension rising along the side of the electrode in the capillary tube by surface tension to a height of 117 μm at frequencies of 0 Hz up to 150 kHz.
Figure 10:
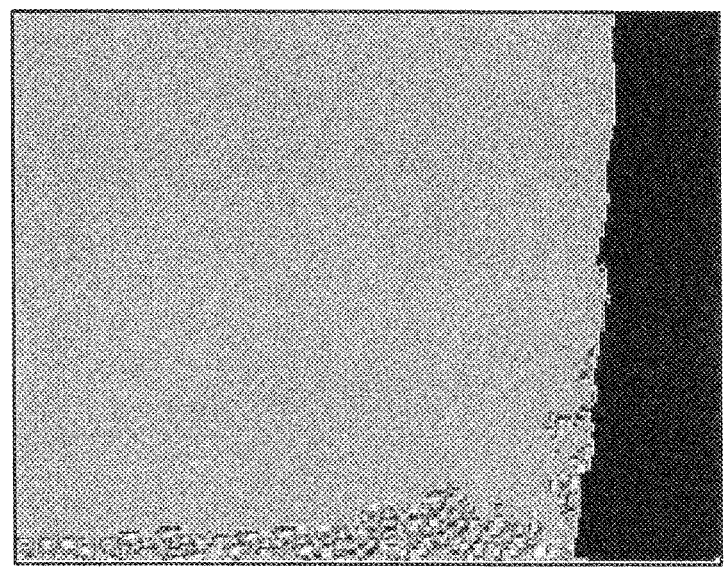
FIG. 10 is a CCD image (side view) showing normal red blood cells in the suspension being repelled down the side of the electrode in the capillary tube at a frequency of $1.45 \times 10^6$ Hz, together with the formation of some chains of red blood cells up to six cells in length.
Figure 11:
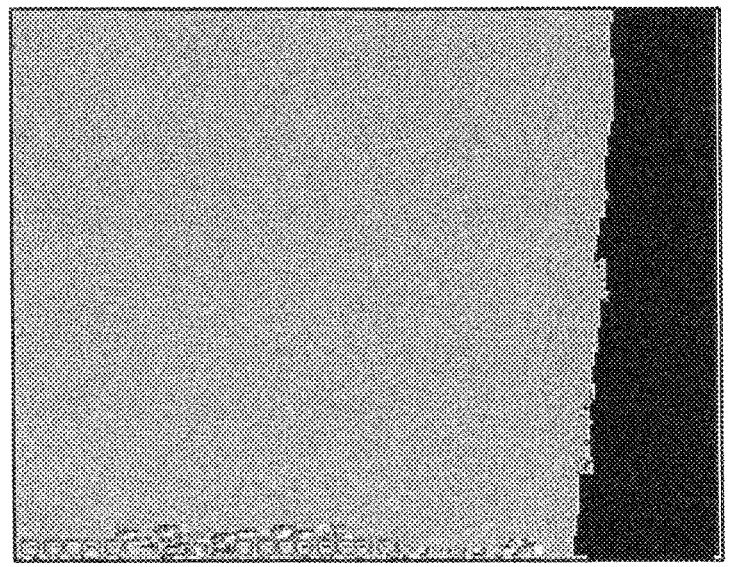
FIG. 11 is a CCD image (side view) showing normal red blood cells in the suspension being repelled down the side of the electrode in the capillary tube to a minimum height of 36 μm at a frequency of $1.5 \times 10^6$ Hz, together with the maximum formation of chains of red blood cells.
Figure 12:
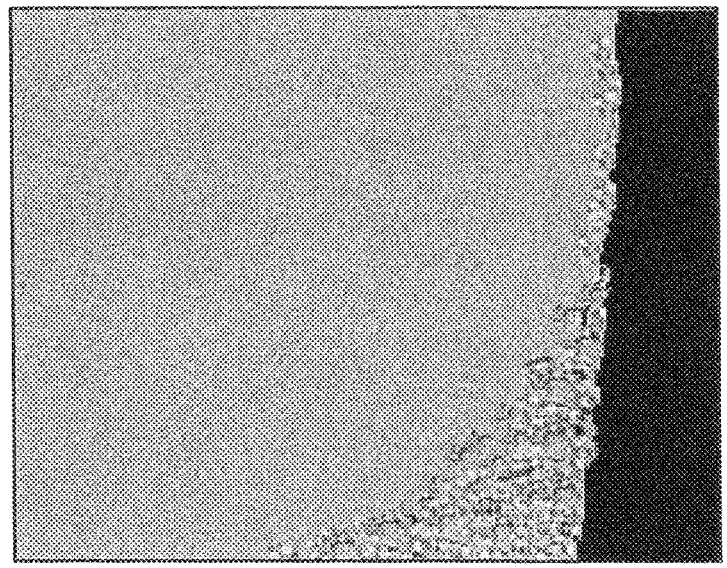
FIG. 12 is a CCD image (side view) showing normal red blood cells in the suspension returned to a random distribution along the side of the electrode in the capillary tube and risen to a height of 112 μm at a frequency of $1 \times 10^7$ Hz, reflecting the increase in frequency.

In the same regard, the side view frames of RBCs-N are shown in FIGS. 9-12. The data shown in these Figures confirm the above mentioned data taken from the top views presented in FIGS. 5-8. A random distribution of RBCs-N around the electrode 18 is illustrated in FIG. 9 when there is no electric field, and the microparticles in the suspension ascend along the metallic electrode 18, by the surface tension effect, up to 117 μm, against the force of gravity. Upon applying an electric field at relatively low frequency, this rise up the electrode 18 holds until a frequency of about f<150 kHz. At 150 kHz, the RBCs-N start to get away from the metallic electrode 18, and the RBCs-N lower to about 88 μm. The net repulsion of RBCs-N continues with a random distribution descending at the side of the electrode 18 until a frequency of 1.45×10$^6$ Hz, when some RBCs form several chains of cells, which are seen clearly in FIG. 10. The height of the RBCs-N suspension attains its minimum value at 36 μm, accompanied with the maximum formation of chains at 1.5×10$^6$ Hz, as seen in FIG. 11. As the frequency of the a.c. field continues to increase, the red blood cells begin to rise alongside the electrode. At 2×10$^6$ Hz, the RBCs-N suspension attains 53 μm, and the formation of the chains decreases rapidly. The rise of RBCs-N suspension attains 67 μm at 5×10$^6$ Hz, where the chains have nearly disappeared. At 8×10$^6$ Hz, rise of RBCs-N suspension attains 99 μm, and the chains have completely disappeared. The rise of RBCs-N suspension continues and attains 112 μm, and a more random distribution is illustrated at 1×10$^7$ Hz, as shown in FIG. 12. Similar to FIG. 7, the data on FIG. 11 show that the minimum rise of RBCs-N suspension at 1.5×10$^6$ Hz corresponds to the minimum disorder that takes place at 1.65×10$^6$ Hz.

The method of detecting leukemia involves testing control samples of normal red blood cells and red blood cells known to be from a patient having leukemia to determine the resonant or critical frequencies for both, and an unknown sample of red blood cells in the apparatus, sweeping the applied a.c. field through 0 Hz to 1×10$^7$ Hz for each sample. When the frequency of the peak of electrical resistance for the unknown sample and/or the frequency at which the CCD images show maximum repulsion of the red blood cells of the unknown sample equal or approximately equal the resonant frequency of the known leukemia red blood cells, the test indicates the presence of leukemic blood cells in the unknown sample.

The present invention is advantageous in that it avoids the Faradic effects by using similar metallic electrodes. Also, it is well known that high intensity nonlinear electro-osmotic micro-vortex is generated around a small conductive ion exchange granule when the ac-electric field attains 25-125 V cm$^{-1}$ in the frequency range near 0.3 Hz. Thus, the present invention avoids the presence of ac-nonlinear electro-kinetic vortex flows in our invention's measurements by keeping our measurements far away from these values of 25-125 Vcm$^{-1}$ and 0.3 Hz. Additionally, the detection of MPs has been carried out using impedance measurements. As it is well known, time-periodic reverse voltage bias across a bipolar membrane is shown to exhibit hysteresis due to transient effects. To prevent water dissociation due this hysteresis in the thin polarized layers, the electric field is kept so low, during all measurements presented in this invention that this hysteresis did not take place in our examples. Accordingly, the present invention overcomes the shortcomings of the prior art and provides a more accurate method of detecting and diagnosing leukemia in a patient.

It is to be understood that the present invention is not limited to the embodiments described above, but encompasses any and all embodiments within the scope of the following claims.

We claim:

1. A method of detecting leukemia, comprising the steps of:
    placing a suspension of red blood cells in a reservoir having a capillary tube partially immersed in the suspension;
    placing a first electrode in the reservoir outside the capillary tube;
    placing a second electrode into the capillary tube, and bringing the second electrode into contact with the surface of the suspension;
    applying an a.c. field to the electrodes;
    sweeping the frequency of the a.c. field between 0 Hz and $1 \times 10^7$ Hz;
    measuring the electrical resistance as a function of frequency between the second electrode and the surface of the suspension; and
    taking top view images of the suspension at the interface between the second electrode and the surface of the suspension with a charge-coupled device (CCD) camera during said sweeping step;
    analyzing the images to determine a resonant frequency at which the red blood cells are repelled from the electrode and exhibit a most-ordered pattern of chains of red blood cells; and
    comparing the resonant frequency with a frequency that is unique to red blood cells obtained from patients with leukemia, leukemia being detected when the frequencies are substantially identical.

2. The method of detecting leukemia according to claim 1, wherein the suspension of red blood cells comprises a suspension of red blood cells in distilled water.

3. The method of detecting leukemia according to claim 1, wherein the capillary tube has an inside diameter of 200 µm.

4. The method of detecting leukemia according to claim 3, wherein each of the electrodes has a diameter of 50 µm.

5. The method of detecting leukemia according to claim 1, further comprising the step of covering the reservoir to prevent evaporation during said sweeping and measuring steps in order to preserve the level of the suspension in the reservoir and avoid development of a temperature gradient normal to the surface due to cooling of the upper surface.

6. The method of detecting leukemia according to claim 1, further comprising the step of maintaining a constant voltage during said sweeping and measuring steps.

7. The method of detecting leukemia according to claim 1, further comprising the steps of:
    performing said placing step through said measuring step for a control sample of normal red blood cells drawn from a healthy patient to determine a resonant frequency of normal red blood cells where the electrical resistance rises to a peak; and
    performing said placing step through said measuring step for a control sample of leukemic red blood cells drawn from a patient known to have leukemia to determine the frequency that is unique to red blood cells obtained from patients with leukemia.

8. The method of detecting leukemia according to claim 1, further comprising the steps of:
    taking side view images of the suspension at the interface between the second electrode and the surface of the suspension with a charge-coupled device (CCD) camera during said sweeping step;
    analyzing the images to determine a resonant frequency at which the red blood cells are repelled downward along the side of the electrode to their lowest height and exhibit a most-ordered pattern of chains of red blood cells; and
    comparing the resonant frequency with the frequency that is unique to red blood cells obtained from patients with leukemia, leukemia being detected when the frequencies are substantially identical.

9. A method of detecting leukemia, comprising the steps of:
    placing a suspension of red blood cells in a reservoir having a capillary tube partially immersed in the suspension;
    placing a first electrode in the reservoir outside the capillary tube;
    placing a second electrode into the capillary tube and bringing the second electrode into contact with the surface of the suspension;
    applying an a.c. field to the electrodes;
    sweeping the frequency of the a.c. field between 0 Hz and $1 \times 10^7$ Hz;
    measuring the electrical resistance as a function of frequency between the second electrode and the surface of the suspension;
    taking side view images of the suspension at the interface between the second electrode and the surface of the suspension with a charge-coupled device (CCD) camera during said sweeping step;
    analyzing the images to determine a resonant frequency at which the red blood cells are repelled downward along the side of the electrode to their lowest height and exhibit a most-ordered pattern of chains of red blood cells; and
    comparing the resonant frequency with a frequency that is unique to red blood cells obtained from patients with leukemia, leukemia being detected when the frequencies are substantially identical.

* * * * *